United States Patent [19]

Chen et al.

[11] Patent Number: 4,792,577
[45] Date of Patent: Dec. 20, 1988

[54] STAIN-RESISTANT NO-MIX ORTHODONTIC ADHESIVE

[75] Inventors: Albert C. Chen, East Brunswick, N.J.; David L. Siegfried, Langhorne; Donald S. Mueller, Newtown, both of Pa.

[73] Assignee: Johnson & Johnson Consumer Products, Inc., New Brunswick, N.J.

[21] Appl. No.: 74,108

[22] Filed: Jul. 16, 1987

[51] Int. Cl.$^4$ .......................... A61K 5/06; C08L 33/08
[52] U.S. Cl. ................................... 523/118; 523/115; 523/116
[58] Field of Search .................... 523/115, 116, 118

[56] References Cited

U.S. PATENT DOCUMENTS

| | | | |
|---|---|---|---|
| 3,895,445 | 7/1975 | Silverman et al. | 433/9 |
| 4,010,545 | 3/1977 | Kilian et al. | 433/9 |
| 4,200,980 | 5/1980 | Johnston | 433/8 |
| 4,297,266 | 10/1981 | Ibsen et al. | 523/115 |
| 4,340,529 | 7/1982 | Lee et al. | 524/854 |
| 4,340,532 | 7/1982 | Lee et al. | 523/219 |
| 4,363,624 | 12/1982 | Johnston | 433/9 |
| 4,500,657 | 2/1985 | Kumar | 522/83 |
| 4,540,723 | 9/1985 | Ying | 523/115 |
| 4,554,336 | 11/1985 | Kidd et al. | 523/109 |
| 4,674,980 | 6/1987 | Ibsen et al. | 523/115 |

*Primary Examiner*—Herbert J. Lilling
*Attorney, Agent, or Firm*—Charles J. Metz

[57] ABSTRACT

A stain resistant no-mix orthodontic adhesive is disclosed. The adhesive comprises:

(a) a first component having a relatively low viscosity and which contains an acrylic or methacrylic diester of ethoxylated bisphenol-A, an acrylic or methacrylic diester of an alkanediol, and benzyl acrylate or methacrylate; and (b) a second component containing a filler and an acrylic or methacrylic diester of ethoxylated bisphenol-A, an acrylic or methacrylic diester of an alkanediol, and benzyl methacrylate or acrylate, said filler being present in an amount within the range of from about 50 to about 80 weight percent of said second component, wherein, one of said first and second components contains a peroxide catalyst and the other of said components contains a tertiary amine activator for said peroxide catalyst.

7 Claims, No Drawings

STAIN-RESISTANT NO-MIX ORTHODONTIC ADHESIVE

The invention relates to a stain-resistant no-mix orthodontic adhesive.

BACKGROUND OF THE INVENTION

The term "no-mix orthodontic adhesives" is used to refer to two-package adhesive systems that are not mixed prior to applying to the tooth to bond an orthodontic bracket thereto. A typical example is an acrylic resin system consisting of two packages; one part contains an acrylic resin and an accelerator and the other contains an acrylic resin and a catalyst. Typically, a "primer" coating of unfilled resin and, e.g., the accelerator, is applied to the surface of the tooth and to the bonding surface of the bracket, and the other part of the two-package system (a filled resin system containing the catalyst) is then interposed between the two primer coats. The accelerator then activates the catalyst when the two parts of the system contact each other, and the resin is thereby cured. Examples of such no-mix systems are described by Lee et al. in U.S. Pat. No. 4,340,529 and by Johnston in U.S. Pat. Nos. 4,200,980 and 4,363,624.

No-mix adhesives seldom achieve the ultimate bond strength achieved by the more conventional two package chemically cured adhesives that are mixed prior to use. However, no-mix adhesives are gaining favor in the orthodontic profession because the no-mix adhesives are easier to use and do provide certain functional advantages. First, a conventional two-part mix adhesive has a finite working time after it has been mixed, usually of the order of 2–3 minutes. Thus, after such an adhesive has been mixed, the dentist must hurry to use it before it sets up. In contrast, the no-mix adhesive is not "mixed" until the paste portion is placed in contact with the liquid ("primer") portion, just as the bracket is being placed. Therefore, the dentist can work with one bracket at a time at a non-hurried pace. In many cases, with mix adhesives, a significant proportion of the mixed formulation sets up before it is used, with resulting waste of material. Also, once the no-mix adhesive has been applied, the setting time is quite short (e.g., 20–45 seconds); therefore, there is less chance that the bracket will drift out of place once it has been positioned on the tooth than is the case with mix adhesives wherein the setting time is longer.

Since the advent of orthodontic brackets made of clear materials such as polycarbonate, and more recently single crystal alumina or clear sapphire, there has been a need to employ bracket adhesives that resist staining from foods and beverages. Obviously the aesthetic advantage of using a clear bracket would be somewhat diminished if the bracket adhesive were to discolor. This invention provides a no-mix orthodontic bracket adhesive that achieves a bond strength equal to or better than current no-mix adhesives that are commercially available, and which resists staining from beverages and foodstuffs significantly better than any of the currently available commercial no-mix orthodontic adhesives.

BRIEF SUMMARY OF THE INVENTION

The invention provides an orthodontic adhesive containing two parts that become active and cure to a stain resistant material when a layer of one of the parts is placed in contact with a layer of the other part, the two parts comprising:

(a) a first component having a relatively low viscosity and which contains an acrylic or methacrylic diester of ethoxylated bisphenol-A or equivalent diester that is free of hydroxyl groups, an acrylic or methacrylic diester of an alkanediol, and benzyl acrylate or methacrylate; and (b) a second component containing essentially the same resin mixture found in the first component and sufficient filler to make a paste, preferably wherein the filler loading is relatively high, wherein one of said first or second components contains a peroxide catalyst such as benzoyl peroxide, and the other of said first or second components contains a tertiary amine activator for said peroxide catalyst.

THE PRIOR ART

In addition to the Lee et al. and the Johnston patents cited above, the relevant prior art includes Ying, U.S. Pat. No. 4,540,723, who discloses a resin system similar to the one used in the adhesive of the invention which contains a monofunctional monomer such as benzyl methacrylate (Ying's resin system is used in a dental restorative composition), and Kumar, U.S. Pat. No. 4,500,657, who discloses resin systems wherein the monomers are free of hydroxyl groups or other functional groups that are relatively hydrophilic. The Kumar patent also relates to dental restorative compositions.

DETAILED DESCRIPTION OF THE INVENTION

The no-mix adhesive of the invention contains two components, a liquid component having a relatively low viscosity and a paste component. Both components can use essentially the same resin formulation, although proportions of the individual monomers of the resin formulation may vary from one component to the other. The first monomer in the resin formulation is preferably ethoxylated bisphenol-A dimethacrylate ("EBDM") or similar diacrylate or dimethacrylate ester that is free of functional groups such as hydroxyl, amino, carboxyl, or the like that impart water-sensitivity. Illustrative examples of such other diesters that can be used include ethoxylated bisphenol-A diacrylate or other alkoxylated bisphenol-A diacrylate or dimethacrylate. The resin formulation also includes a reactive diluent monomer such as an alkanediol diacrylate or dimethacrylate. Illustrative examples of such reactive diluents include 1,6-hexanediol dimethacrylate, 1,8-octanediol dimethacrylate, and the equivalent diacrylate esters. The final monomer in the resin formulation is benzyl methacrylate or acrylate.

The proportion of the monomers in the resin is not narrowly critical. Broadly, the proportions of the monomers in the resin will usually be within the ranges given in the following table, which also displays the viscosities (at 23° C.) of the two components:

| PERCENTAGES, BASED ON RESIN WEIGHT | | |
| --- | --- | --- |
| | BROAD | PREFERRED |
| PRIMER | | |
| EBDM (or equivalent) | 40–90 | 70–80 |
| Reactive Diluent | 5–30 | 5–10 |
| Benzyl acrylate or methacrylate | 5–30 | 15–20 |

-continued

| PERCENTAGES, BASED ON RESIN WEIGHT | | |
| --- | --- | --- |
|  | BROAD | PREFERRED |
| Viscosity, centipoises | 100–2000 | 200–600 |
| PASTE | | |
| EBDM (or equivalent) | 40–90 | 70–80 |
| Reactive Diluent | 5–30 | 5–10 |
| Benzyl acrylate or methacrylate | 5–30 | 15–20 |
| Viscosity, centipoises | 50,000–500,000 | 100,000–300,000 |

The polymerization catalyst is added to one of the components, and the catalyst activator or accelerator is added to the other. Preferably, the activator is added to the primer formulation. The activator is usually an aromatic tertiary amine such as N,N-bis($\beta$-hydroxyethyl)-2-methyl-p-toluidine, N,N-diethyl-p-toluidine, N,N-bis($\beta$-hydroxyethyl)-p-toluidine, ethyl 4-(N,N-dimethylamino)benzoate, or the like. The accelerator is used in relatively large proportions (compared to the amount usually used in two-package mix formulations), usually in the range of from about 2 to about 10 weight percent of the total resin weight in the component to which it is added. To ensure that the accelerator does not precipitate during storage, it is useful to warm the resin slightly while adding the accelerator (e.g., to about 60°–70° C., which is above the melting point of the accelerator), to mix the heated resin/accelerator mixture for about 15–30 minutes, and to then filter the resin containing the accelerator through a 400-mesh screen to make sure that no nucleation particles are present in the resin.

The polymerization catalyst is added to the other component, usually the past component. Usually, the catalyst will be a peroxide such as benzoyl peroxide, methyl ethyl ketone peroxide, or the like. The peroxide is used in catalytically effective amounts, e.g., from about 1 to about 5 weight percent, based on the weight of the resin in the component to which it is added. A stabilizer such as an alkylphenol is included in the component that contains the peroxide.

The conventional fillers can be used in the paste component. These include colloidal silica, finely divided glass (preferably acid washed, heat treated barium or strontium glass, as described by Denton et al. in U.S. Pat. No. 4,492,777), finely divided quartz, and the like. The acid washed and heat treated glass powders described in the cited Denton et al. patent are heated at an elevated temperature (below the sintering temperature of the glass) sufficient to cause a significant reduction in the specific surface area of the glass powder. The Denton et al. patent is incorporated herein by reference. Preferably, the filler is silane-treated to promote bonding to the resin, as is conventional. The filler is preferably used in relatively high proportions, such as from about 100 to about 400 parts by weight per hundred parts by weight of resin in the paste.

The preferred way to use the no-mix adhesive of the invention is to apply the primer to the clean bonding surface of the orthodontic bracket and to the etched surface of the tooth to which the bracket is to be applied, and to interpose a layer of the paste between the two layers of primer as the bracket is applied. The resin will set up in a rather short period of time (15–30 seconds), so the bracket need only be held in place by the dentist for this short period of time. In fact, the viscosity of the paste component is such that the bracket will not ordinarily drift or shift its position after placement, even prior to setting of the adhesive.

The experimental section below illustrates a specific formulation of the invention, and compares its mechanical properties and stain resistance with a number of commercially available no-mix orthodontic adhesives.

The no-mix adhesive of the invention used in the experimental section had the following formulation:

|  | Parts, by weight |
| --- | --- |
| PRIMER Components | |
| EBDM | 70 |
| 1,6-hexanediol dimethacrylate | 10 |
| Benzyl methacrylate | 20 |
| N,N—bis($\beta$-hydroxyethyl)-2-methyl-p-toluidine | 7.5 |
| PASTE COMPONENTS | |
| Resin portion of paste | |
| EBDM | 80 |
| 1,6-hexanediol dimethacrylate | 5 |
| Benzyl methacrylate | 15 |
| Butylated hydroxy-toluene (stabilizer) | 0.03 |
| Benzoyl peroxide | 2.0 |
| PASTE Formulation | |
| Resin, described above | 100 |
| Glass filler[1] | 285 |
| Colloidal silica filler[2] | 15 |

[1]Finely divided (0–13 microns) acid washed, heat treated barium glass treated with 1.5 weight percent gamma-methacryloxypropyltrimethoxysilane (A-174 Silane)
[2]Aerosil OX-50, treated with 3.0 weight percent A-174 Silane. OX-50 has an average particle size of 0.05 micron.

The bond strength of the no-mix formulation described above (Example 1) was evaluated, and was compared with the bond strengths of four commercial no-mix adhesives (Controls A–D).

The primer components of three of the four commercial no-mix adhesives were analyzed for their components by HPLC, with the following results:

|  | AREA UNDER PEAK, PERCENT | | |
| --- | --- | --- | --- |
| COMPONENT | CONTROL A | CONTROL C | CONTROL D |
| N,N—bis($\beta$-hydroxyethyl)-p-toluidine | 69.5 | 47.6 | 40.5 |
| Unknown 1 | — | 8.3 | 10.5 |
| Triethylene glycol dimethacrylate | 15.0 | 2.5 | 3.0 |
| Unknown 2 | — | 2.6 | — |
| Bis-GMA | 4.1 | 12.6 | 19.5 |
| Bisphenol-A dimethacrylate | — | 5.9 | 8.4 |

The following was also determined for the paste components:

| FILLER TYPE | Quartz | Silica | Quartz |
| --- | --- | --- | --- |
| Percent Solids | 40.6 | 64.0 | 69.1 |

The bond strength testing was carried out as follows:

Metal brackets were used. They were bonded to phosphoric acid etched bovine enamel by coating the enamel and the bonding surface of the bracket with the primer portion of the formulation, and then the paste portion was applied to the primed enamel and the primed bracket was immediately placed on the tooth and held in place for 5 seconds. Each bovine enamel piece was embedded in one end of an acrylic cylinder whose dimensions were 1½ cm in diameter by 2.8 cm long. The enamel surfaces were polished with 600 grit silicone carbide grinding paper prior to etching with phosphoric acid for 60 seconds. The surfaces were rinsed with tap water for 60 seconds after the etching. Bond strengths were measured after 5 minutes, 10 minutes, 60 minutes, and 24 hours.

The 5, 10, and 60 minute tests were carried out on dry samples, the 24 hour tests were carried out on samples that were immersed in water at 37° C. about one hour after placement and kept there for the remainder of the 24 hours. The bond strength was tested in shear as follows:

The acrylic cylinders containing the bracket bonded to enamel were clamped in the test piece holder of an Instron Laboratory tester so that a flat striker rod impinged upon the tie wings of the bracket at right angles. The Instron was turned on (a crosshead speed of 0.5 mm per minute was used), and the force required to break the bracket away from the substrate was recorded. Bond strength equals force at break divided by bonding area of the bracket, and is expressed in MPa's.

The table below displays the results of the bond strength testing. Each number is the average of 12 samples.

TABLE I

| | BOND STRENGTH RESULTS | | | | | | | |
|---|---|---|---|---|---|---|---|---|
| | 5 min. | | 10 Min. | | 60 Min. | | 24 Hrs. | |
| No-Mix Adhesives | Mean | S.D.[1] | Mean | S.D. | Mean | S.D. | Mean | S.D. |
| Example 1 | 8.3 | 1.3 | 10.8 | 0.9 | 12.3 | 1.5 | 12.6 | 1.5 |
| Control A | 9.0 | 1.3 | 10.9 | 1.1 | 12.9 | 1.2 | 12.5 | 1.3 |
| Control B | 8.6 | 1.3 | 10.0 | 1.6 | 11.5 | 1.4 | 11.6 | 1.6 |
| Control C | 7.7 | 2.1 | 10.5 | 1.5 | 11.0 | 1.2 | 11.2 | 2.1 |
| Control D | 6.4 | 1.0 | 9.3 | 1.0 | 11.4 | 1.5 | 11.0 | 0.9 |

[1]S.D. = Standard Deviation

Each of the no-mix adhesives that were tested for bond strength were also tested for stain resistance by the following procedure:

Each formulation was mixed (in proportions of about 1:1 primer-paste, by volume) and immediately molded into a small disc-shaped article (dimensions were 1 mm thick, 10 mm diameter). Two samples of each test adhesive were then immersed in each of water, coffee, or tea for four weeks at 50° C. The test specimens were rated 1 (least staining) through 5 (most staining) for each test liquid. The ratings are comparisons with a control of the same adhesive stored in water at 5° C. for the same period of time. (None of the controls exhibited any staining when stored in water at 5° C.) The results were as follows:

TABLE II

| | STAIN RATING IN | | |
|---|---|---|---|
| | WATER | COFFEE | TEA |
| Example 1 | 1 | 1.3 | 1.5 |
| Control A | 3.3 | 2.5 | 2.2 |
| Control B | 2.7 | 2.5 | 2.7 |
| Control C | 3.3 | 4.0 | 4.0 |
| Control D | 4.7 | 4.7 | 4.7 |

Each number is the average of six ratings that were made by six members of a color panel.

What is claimed is:

1. An orthodontic adhesive composition that becomes reactive and sets to a stain resistant material when a layer of one component is placed in contact with a layer of the other component, which consists essentially of:
    (a) a first component having a relatively low viscosity and which contains an acrylic or methacrylic diester of ethoxylated bisphenol-A, an acrylic or methacrylic diester of an alkanediol, and benzyl acrylate or methacrylate; and
    (b) a second component containing a filler and an acrylic or methacrylic diester of ethoxylated bisphenol-A, an acrylic or methacrylic diester of an alkanediol, and benzyl methacrylate or acrylate, said filler being present in an amount within the range of from about 50 to about 80 weight percent of said second component,
    wherein, one of said first and second components contains a peroxide catalyst and the other of said components contains a tertiary amine activator for said peroxide catalyst.

2. The adhesive formulation of claim 1 wherein both said components contained ethoxylated bisphenol-A dimethacrylate, 1,6-hexanediol dimethacrylate, and benzyl methacrylate.

3. The adhesive formulation of claim 1 wherein the tertiary amine activator is contained in said first component.

4. The adhesive formulation of claim 2 wherein the tertiary amine activator is contained in said first component.

5. The adhesive formulation of any of claims 1–4 wherein the filler includes colloidal silica and finely divided quartz or finely divided barium or strontium glass that has been acid washed and heat treated at an elevated temperature sufficient to cause a significant reduction in the specific surface area of the glass powder.

6. The adhesive formulation of any of claims 1–4 wherein the tertiary amine activator is N,N-bis($\beta$-hydroxyethyl)-2-methyl-p-toluidine.

7. The adhesive formulation of claim 5 wherein the tertiary amine activator is N,N-bis($\beta$-hydroxyethyl)-2-methyl-p-toluidine.

* * * * *